(12) United States Patent
Ujihara et al.

(10) Patent No.: US 7,012,679 B2
(45) Date of Patent: Mar. 14, 2006

(54) INSPECTION METHOD AND INSPECTION SYSTEM OF SURFACE OF ARTICLE

(75) Inventors: Takashi Ujihara, Tokyo (JP);
Hirotoshi Inomata, Tokyo (JP); Isao Fujita, Tokyo (JP)

(73) Assignee: Dowa Mining Co., Ltd., Tokyo (JP)

( * ) Notice: Subject to any disclaimer, the term of this patent is extended or adjusted under 35 U.S.C. 154(b) by 406 days.

(21) Appl. No.: 10/346,065

(22) Filed: Jan. 17, 2003

(65) Prior Publication Data

US 2003/0142298 A1 Jul. 31, 2003

(30) Foreign Application Priority Data

Jan. 31, 2002 (JP) ............................. 2002-023729

(51) Int. Cl.
*G01N 21/00* (2006.01)

(52) U.S. Cl. .................................................. 356/237.1
(58) Field of Classification Search ............ 356/237.1, 356/237.2–237.5; 382/141–151
See application file for complete search history.

(56) References Cited

U.S. PATENT DOCUMENTS

| 4,467,350 A | * | 8/1984 | Miller ......................... 348/133 |
| 4,487,322 A | * | 12/1984 | Juvinall ....................... 209/526 |
| 5,754,678 A | * | 5/1998 | Hawthorne et al. ......... 382/149 |
| 6,021,380 A | * | 2/2000 | Fredriksen et al. ........... 702/35 |

FOREIGN PATENT DOCUMENTS

| CA | 2277855 A | 1/2001 |
| CN | 1177733 A | 4/1998 |

* cited by examiner

*Primary Examiner*—Layla G. Lauchman
*Assistant Examiner*—Juan D. Valentin, II
(74) *Attorney, Agent, or Firm*—Rader, Fishman & Grauer PLLC

(57) ABSTRACT

The present invention is a method for inspecting a surface of an article through an image thereof by photographing a surface to be inspected of the article with a CCD camera, in which the surface of the article is inspected by selecting two arbitrary pixels from among pixels showing the surface to be inspected in the image and comparing the two pixels. When the two pixels are selected, for example, pixels in point-symmetry or line symmetry can be selected. Further, the two selected pixels are compared, for example, in brightness.

7 Claims, 6 Drawing Sheets

INSPECTION METHOD AND INSPECTION SYSTEM OF SURFACE OF ARTICLE

BACKGROUND OF THE INVENTION

1. Field of the Invention

The present invention relates to a method and an apparatus each for inspecting an appearance of an article through a photographed image of a surface thereof.

2. Description of the Related Art

As a method for inspecting the state of a surface of an article, various methods are generally known, and a method is employed, in particular, which inspects the state of the surface of the article by photographing the article with a CCD camera and processing its image. In this case, for example, pixels at about ten points are selected from among pixels showing a surface to be inspected in the image photographed with the CCD camera, and a mean value of brightnesses of the pixels is set as a standard value, so that the brightness of a pixel at a point to be measured is compared to the standard value, thereby inspecting the state of the surface of the article.

However, such a conventional inspection method has a problem that inspection results do not stable because of changes in the surface state of the article, changes in the external environment such as sunlight, room light or the like, the presence or absence of illumination for photographing the image and so on. Further, elimination of the influence of the external environment to stable the inspection results requires a large investment.

SUMMARY OF THE INVENTION

The present invention is made in consideration of the above points, and it is an object of the invention to provide a method and a system each capable of stably inspecting the state of a surface of an article without influence of an external environment and the like.

The present inventors photographed plated surfaces of disc-shaped magnets made of a rare-earth metal with a CCD camera, observed nonuniformity of color, smears, swells, chips and so on in their images, and studied in various ways. As a result, the inventors found the fact that the optically measured value of a surface to be inspected (a plated surface), in particular, its brightness, differs depending on the external environment and the kind of an article. However, in the image photographed with the CCD camera, brightnesses of pixels showing the surface to be inspected exhibit almost fixed values to be in an normal distribution of about ±20% when the surface to be inspected is a flat surface or a curved surface with a small curvature, while when there are defects such as smears, swells, hair cracks or the like, the brightnesses of pixels showing defective points exhibit unusual values.

Based on the above realization, according to the present invention, an inspection method is provided which is a method for inspecting a surface of an article through an image thereof by photographing a surface to be inspected of the article with a CCD camera, characterized by selecting two arbitrary pixels from among pixels showing the surface to be inspected in the image and comparing the two pixels to inspect the surface of the article.

It is preferable that this inspection method compares all of the pixels showing the surface to be inspected. Further, it is possible that when the two pixels are selected, pixels in point-symmetry or line symmetry are selected. The two selected pixels are compared, for example, in brightness. In this case, a ratio between the brightnesses of the two selected pixels is obtained, and when a predetermined number of pixels having ratios outside a predetermined range exist continuously, a state of the surface of the article can be judged to be defective. It should be noted that when the surface to be inspected of the article is photographed with the CCD camera, the surface to be inspected may be illuminated by a light source.

Further, according to the present invention, an inspection system is provided which is characterized by including: a light source for illuminating a surface to be inspected of the article; a CCD camera for photographing the surface to be inspected of the article; and a controller for selecting two arbitrary pixels from among pixels showing the surface to be inspected in the photographed image and comparing the two pixels to inspect the surface of the article. In this case, the system may further include a sorter for sorting the articles in accordance with inspection results by the controller.

According to the present invention, it becomes possible to stably inspect an appearance of an article.

DETAILED DESCRIPTION OF THE INVENTION

Figure 1:
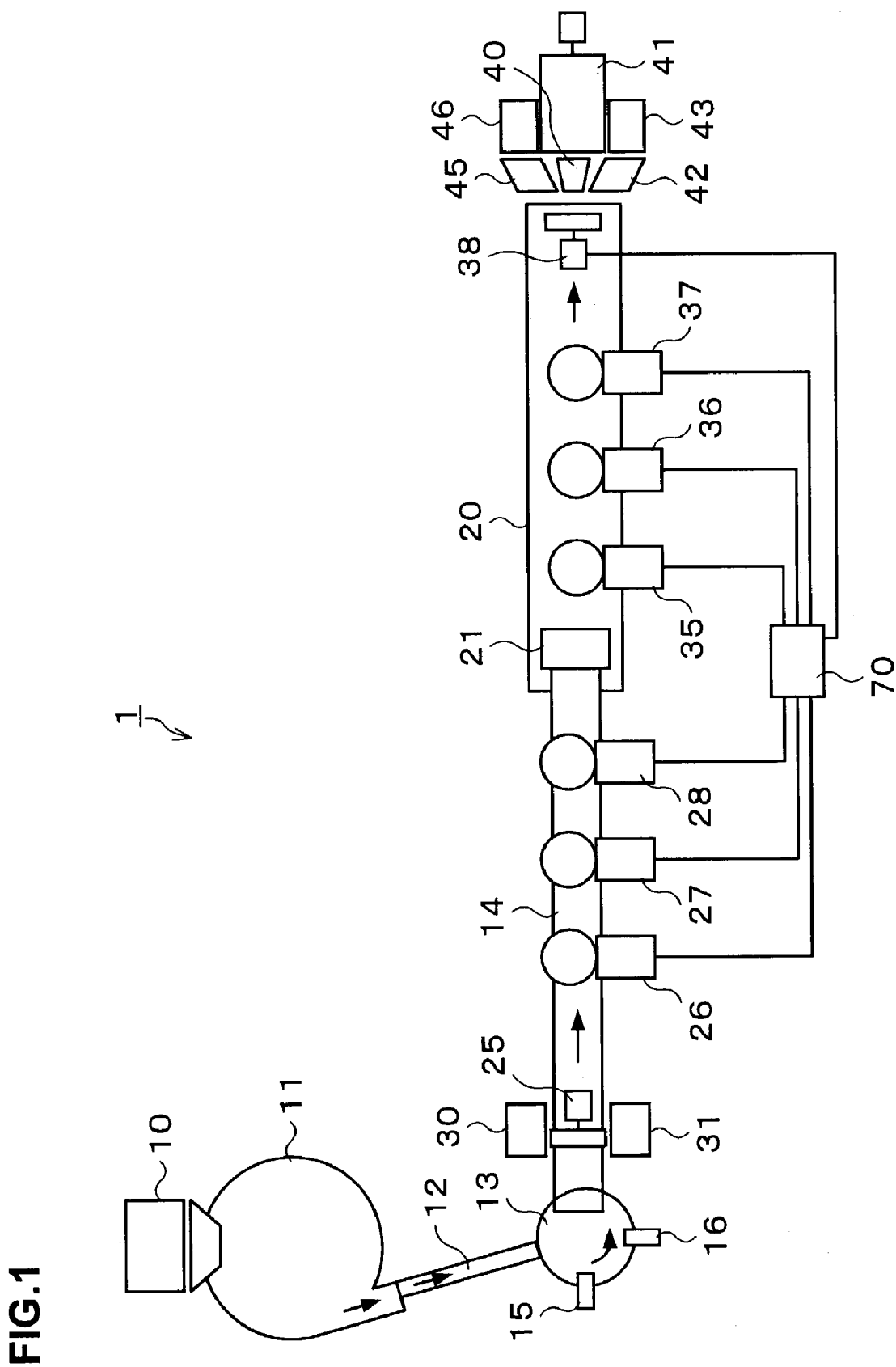
FIG. 1 is a plan view showing a general configuration of an inspection system according to an embodiment of the present invention.

Hereinafter, a preferred embodiment of the present invention is described with reference to the drawings. FIG. 1 is a plan view showing a general configuration of an inspection system 1 according to the embodiment of the present invention. In this embodiment, the inspection system 1 is configured to sequentially inspect appearances of works W each composed of an Nd—Fe—B—C sintered magnet that is one example of an article.

The work (rare-earth magnet) W is in a circular or square plate shape. Such a work W in a plate shape is formed by cutting, into slices, a sintered article in a circular rod or square rod obtained by burning, and is, for example, several millimeters in thickness and about 10 mm in diameter or in length of one side. Therefore, both of a front face W1 and a back face W2 of the work W are formed into cut surfaces.

In the inspection system 1 shown in FIG. 1, the works W are fed from a hopper 10, through an aligning feeder 11 and a linear feeder 12, and taken out one by one by a delivery apparatus 13, so that the works W are fed one by one to a start part of a first conveyer 14 (the left end of the first carriage conveyer 14 in FIG. 1). The aligning feeder 11 is designed to exert vibration on the works W fed from the hopper 10 to align the works W to the attitudes that their front faces W1 direct upward and to deliver them to the next linear feeder 12. The delivery apparatus 13 rotates in a counter clockwise direction in FIG. 1, so that the thickness of the work W is checked by two thickness checkers 15 and 16 during the carriage thereby.

The first conveyer 14 carries the work W delivered from the delivery apparatus 13 with the front face W1 directing upward from its start part toward its termination part (rightward in FIG. 1). To the termination part of the first conveyer 14 (the right end of the first conveyer 14 in FIG. 1), a start part of a second conveyer 20 (the left end of the second conveyer 20 in FIG. 1) is connected, so that the first conveyer 14 and the second conveyer 20 constitute a carrier for carrying the works W.

At a connecting part between the termination part of the first conveyer 14 and the start part of the second conveyer 20, a reversing apparatus 21 is disposed which reverses the work W, that is, turns it over. The reversing apparatus 21 reverses the work W delivered from the first conveyer 14 to bring the work W into the attitude that the back face W2 thereof directs upward. The second conveyer 20 carries the work W which has been brought into the attitude that the front face W2 directs upward by the reversing apparatus 21 from its start part toward its termination part (rightward in FIG. 1).

Along the first conveyer 14, a sorter 25 and three inspection means 26, 27 and 28 which inspect the appearance on a side of the front face W1 of the work W are disposed. The sorter 25 is designed to permit the work W, which has been judged to have a thickness within a predetermined range by the inspections by the thickness checkers 15 and 16, to be carried, as it is, rightward in FIG. 1 by the first conveyer 14, while permitting the work W, which has been judged to have a thickness beyond the predetermined range, to be discharged to a region 30 and the work W, which has been judged to have a thickness below the predetermined range, to be discharged to a region 31. This allows only the works W having a thickness within the predetermined range to be fed to the next inspection means 26, 27 and 28.

By the way, along the second conveyer 20, three inspection means 35, 36 and 37 which inspect the appearance on a side of the back face W2 of the work W and a sorter 38 are disposed. The sorter 38 is designed to permit the work W, which has been judged to have a normal appearance by the inspections by the inspection means 26, 27 and 28 disposed along the first conveyer 14 and the inspection means 35, 36 and 37 disposed along the second conveyer 20, to be carried out through a chute 40 into a storage region 41 at the termination part of the second conveyer 20, while permitting the work W, which has been judged to have a defective appearance, to be carried out through a chute 42 into a region 43 at the termination part of the second conveyer 20, and the work W, whose appearance could not been judged to be normal, to be carried out through a chute 45 into a region 46 at the termination part of the second conveyer 20.

Figure 2:
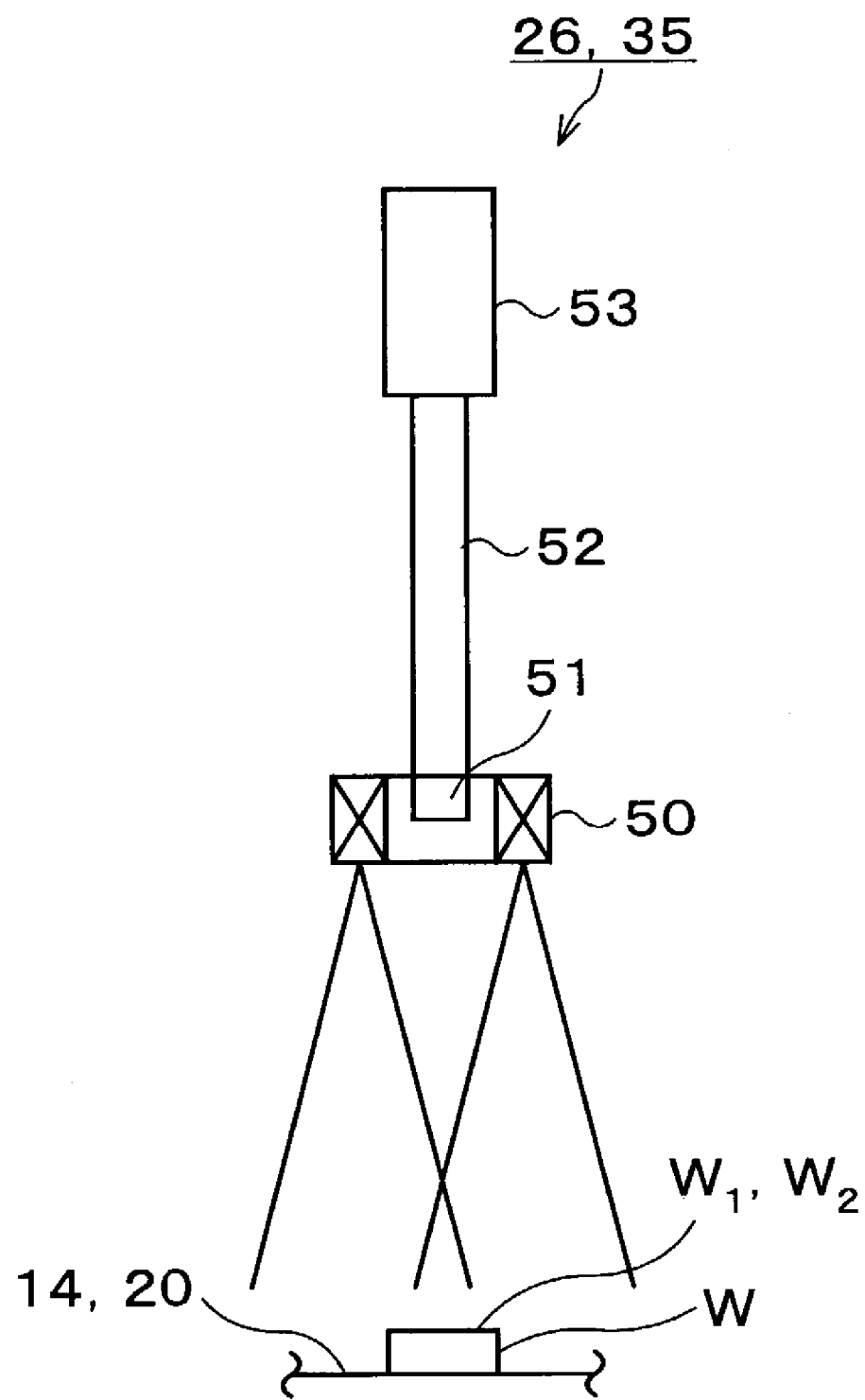
FIG. 2 is an explanatory view of an inspection means.

The inspection means 26 disposed along the first conveyer 14 and the inspection means 35 disposed along the second conveyer 20 have similar configurations, and FIG. 2 is an explanatory view of the inspection means 26 and 35. A light source 50 is disposed above the work W which is carried by the first conveyer 14 or the second conveyer 20 to illuminate the work W from almost directly above. The light source 50 is in a ring shape, and light is applied from the light source 50 to the work W and reflected by the work W to be incident on a conversion lens 51, which is disposed at the center of the light source 50, and passes through a zoom lens 52, so that an image of the work W is photographed with a CCD camera 53. In each of the inspection means 26 and 35, the conversion lens 51, the zoom lens 52 and the CCD camera 53 are all located at positions directly above the work W (in a manner to be perpendicular to the front face W1 of the work W in the inspection means 26 and perpendicular to the back face W2 in the inspection means 35). As described above, the inspection means 26 photographs a surface to be inspected (the front face W1) from a perpendicular (directly above) direction with respect to the front face W1 of the work W which is carried by the first conveyer 14, and the inspection means 35 photographs a surface to be inspected (the back face W2) from a perpendicular (directly above) direction with respect to the back face W2 of the work W which is carried by the second conveyer 20.

Figure 3:
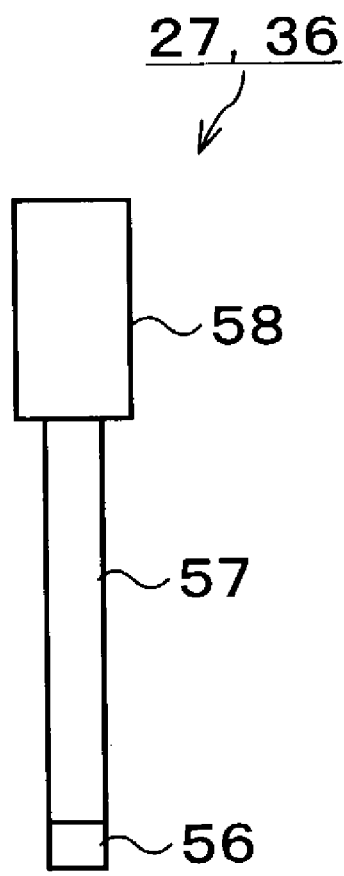
FIG. 3 is an explanatory view of an inspection means having a light source with a large diameter.
Figure 3:
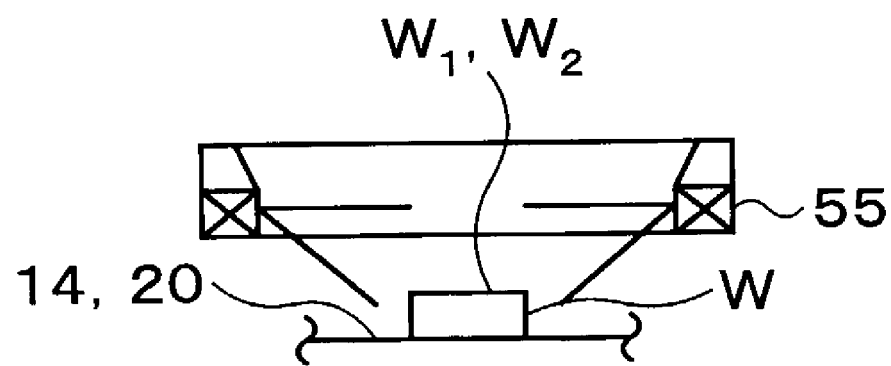

Further, the inspection means 27 disposed along the first conveyer 14 and the inspection means 36 disposed along the second conveyer 20 also have configurations basically similar to those of the inspection means 26 and 35 which are explained in FIG. 2. As shown in FIG. 3, a light source 55 in a ring shape illuminates the work W, and light thereof reflected by the work W is incident on a conversion lens 56 and passes through a zoom lens 57, so that an image of the work W is photographed with a CCD camera 58. The conversion lens 56, the zoom lens 57 and the CCD camera 58 are all located at positions directly above the work W (in a manner to be perpendicular to the front face W1 of the work W in the inspection means 27 and perpendicular to the back face W2 in the inspection means 36). The inspection means 27 photographs the work W from a perpendicular direction with respect to the front face W1 of the work W which is carried by the first conveyer 14, and the inspection means 36 photographs the work W from a perpendicular direction with respect to the back face W2 of the work W which is carried by the second conveyer 20. However, in the inspection means 27 and 36, the light source 55 is large in diameter (as compared to the light source 50) so as to apply light to an outer peripheral part of the work W from the surrounding of the work W. The illustrated embodiment is configured such that light is applied downward at an angle of 45° with respect to the outer peripheral part of the work W. This allows the light applied from the light source 55 to be reflected by the outer peripheral part of the work W, so that the CCD camera 58 photographs the outer peripheral part of the work W.

Figure 4:
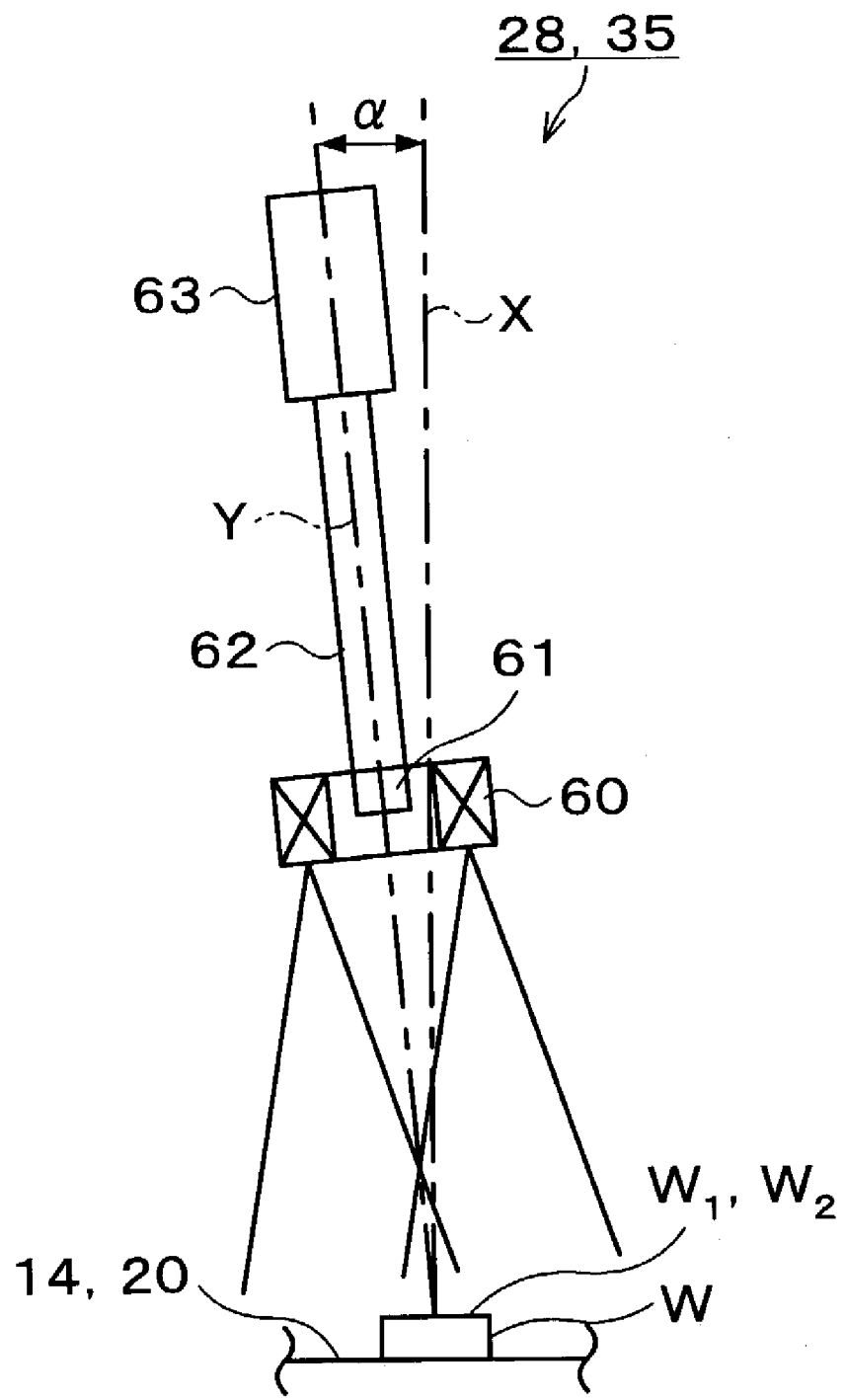
FIG. 4 is an explanatory view of an inspection means with an inclined optical axis.

Furthermore, the inspection means 28 disposed along the first conveyer 14 and the inspection means 37 disposed along the second conveyer 20 also have configurations basically similar to those of the inspection means 26 and 35 which are explained in FIG. 2. As shown in FIG. 4, a light source 60 in a ring shape illuminates the work W, and light thereof reflected by the work W is incident on a conversion lens 61 and passes through a zoom lens 62, so that an image of the work W is photographed with a CCD camera 63. However, while the previously explained inspection means 26 and 35 and inspection means 27 and 36 in which the conversion lenses 51 and 56, the zoom lenses 52 and 57, and the CCD cameras 53 and 58 are all located at positions directly above the work W (in a manner to be perpendicular to the front face W1 or the back face W2 of the work W), the inspection means 28 and 37 are different therefrom in the following point. The point is, as shown in FIG. 4, that the light source 60, the conversion lens 61, the zoom lens 62, and the CCD camera 63 are all located with an optical axis Y, which is inclined at an angle of only α° with respect to an X direction perpendicular to the front face W1 or the back face W2 of the work W, as a center. In this case, the inclined angle 60 is, for example, about 5° to about 10°.

Note that as the light sources 50 of the inspection means 26 and 35 and the light sources 60 of the inspection means 28 and 37, for example, ring illumination of a halogen lamp is used, and as the light sources 55 of the inspection means 27 and 36, illumination by internal-circle irradiation of a halogen lamp is used.

Further, in the inspection means 26 and 35, the inspection means 27 and 36, and the inspection means 28 and 37, for example, a lens by the name of CV-05 (0.5 magnification) or CV-025 (0.25 magnification) manufactured by SEIWA OPTICAL is used as the conversion lenses 51, 56 and 61. In this case, it is preferable to change lenses for use according to the size of the work W, inspection standards and so on in such a manner that CV-025 (with a magnification of 0.25) lens is used for a work W in a point-symmetric shape having a maximum diameter equal to or smaller than 32 φ, and CV-05 (with a magnification of 0.5) lens is used for a work W in a point-symmetric shape having a maximum diameter equal to or smaller than 16 φ.

Further, in the inspection means 26 and 35, the inspection means 27 and 36, and the inspection means 28 and 37, for example, a high resolution zoom lens by the name of MS-501 (0.75 to 4.5) manufactured by SEIWA OPTICAL is used as the zoom lenses 52, 57 and 62. As the CCD cameras 53, 58 and 63, for example, CS3910 (with a resolution of 1280×1030) manufactured by TOKYO ELECTRONIC INDUSTRY, FC-1300 (with a resolution of 1280×1030) manufactured by TAKENAKA SYSTEM, XC-7500 (with a resolution of 512×480) manufactured by Sony or the like is used. Note that it is preferable to use FHC-331LV manufactured by Fast as an image input board for CS3910 manufactured by TOKYO ELECTRONIC INDUSTRY and FC-1300 manufactured by TAKENAKA SYSTEM, and RICE-001 manufactured by Fast as an image input board for XC-7500 manufactured by Sony.

As show in FIG. 1, the images photographed by the inspection means 26 and 35, the inspection means 27 and 36, and the inspection means 28 and 37 are inputted to a controller 70. The controller 70 inspects, as described later, the surface of the work W through the images thus inputted, and controls, based on the inspection results, the sorter 38 which is disposed at the termination part of the second conveyer 20. This allows only the work W having a normal appearance to be discharged to the storage region 41, the work W having a defective appearance to be discharged to the region 43, and the work W whose appearance could not be judged to be discharged to the region 46 as previously described.

In the inspection system 1 configured as described above, the works W brought into the attitude that the front faces W1 direct upward are fed one by one by the delivery apparatus 13 to the start part of the first conveyer 14. Then, only the works W having a thickness within the predetermined range are carried, as they are, rightward in FIG. 1 by the first conveyer 14.

Figure 5:
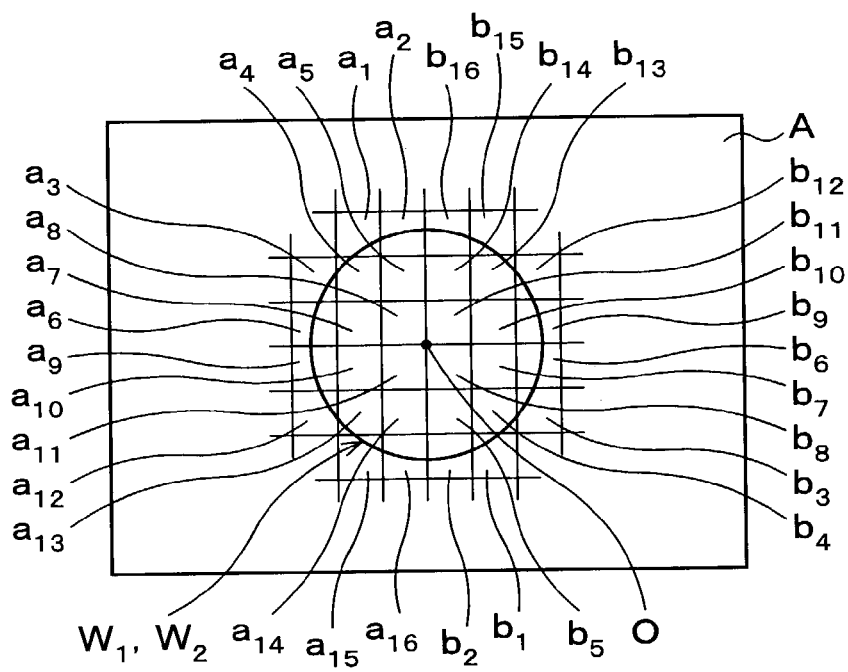
FIG. 5 is an explanatory view of a state of selecting two pixels which are point-symmetric about a center point of a work having a surface to be inspected in a circular shape.

During this carriage, the appearance on the side of the front face W1 of the work W is inspected by the inspection means 26, 27 and 28. More specifically, the work W is first illuminated by the light source 50 of the inspection means 26, and an image of the front face W1 of the work W is photographed with the CCD camera 53 and inputted into the controller 70. An image A of the front face W1 of the work W thus photographed with the CCD camera 53 and inputted into the controller 70 presents a surface to be inspected (the front face W1 of the work W) in a circular shape as shown in FIG. 5 when, for example, the front face W1 of the work W is in a circular shape, or presents a surface to be inspected (the front face W1 of the work W) in a square shape as shown in FIG. 6 when, for example, the front face W1 of the work W is in a square shape.

Then, the controller 70 selects two arbitrary pixels a and b from among pixels showing the surface to be inspected (the front face W1 of the work W) in this image A and compares the two pixels, thereby inspecting the front face W1 of the work W. In this event, if the surface to be inspected (the front face W1 of the work W) is in a point-symmetric shape such as a circular shape, two pixels a and b which are point-symmetric about a center point O as shown in FIG. 5 are individually selected and compared to each other on a set basis. Specifically explaining the example shown in FIG. 5, a pixel a1 and a pixel b1 are compared to each other, a pixel a2 and a pixel b2 are compared to each other, a pixel a3 and a pixel b3 are compared to each other, a pixel a4 and a pixel b4 are compared to each other, a pixel a5 and a pixel b5 are compared to each other, a pixel a6 and a pixel b6 are compared to each other, a pixel a7 and a pixel b7 are compared to each other, a pixel a8 and a pixel b8 are compared to each other, a pixel a9 and a pixel b9 are compared to each other, a pixel a10 and a pixel b10 are compared to each other, a pixel a11 and a pixel b11 are compared to each other, a pixel a12 and a pixel b12 are compared to each other, a pixel a13 and a pixel b13 are compared to each other, a pixel a14 and a pixel b14 are compared to each other, a pixel a15 and a pixel b15 are compared to each other, and a pixel a16 and a pixel b16 are compared to each other. Thus, all of the pixels a1 to a16 and the pixels b1 to b16, which show the surface to be inspected (the front face W1 of the work W), are compared to each other.

Figure 6:
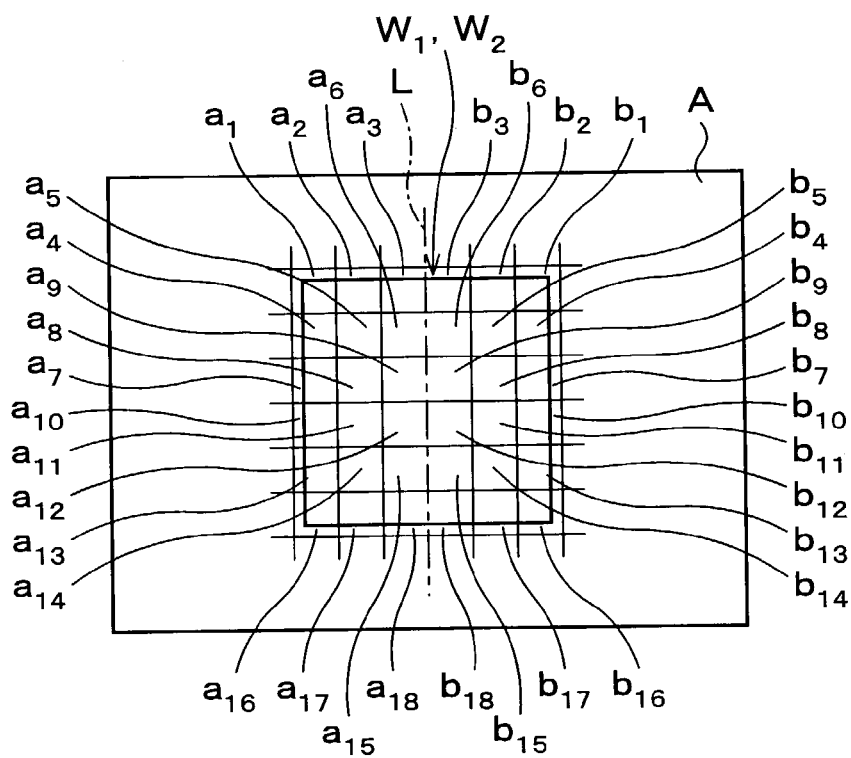
FIG. 6 is an explanatory view of a state of selecting two pixels which are line-symmetric about a center line of a work having a surface to be inspected in a square shape.

If the surface to be inspected (the front face W1 of the work W) is in a line-symmetric shape such as a square shape, two pixels which are line-symmetric about a center line L as shown in FIG. 6 are individually selected and compared to each other on a set basis. Specifically explaining the example shown in FIG. 6, a pixel a1 and a pixel b1 are compared to each other, a pixel a2 and a pixel b2 are compared to each other, a pixel a3 and a pixel b3 are compared to each other, a pixel a4 and a pixel b4 are compared to each other, a pixel a5 and a pixel b5 are compared to each other, a pixel a6 and a pixel b6 are compared to each other, a pixel a7 and a pixel b7 are compared to each other, a pixel a8 and a pixel b8 are compared to each other, a pixel a9 and a pixel b9 are compared to each other, a pixel a10 and a pixel b10 are compared to each other, a pixel a11 and a pixel b11 are compared to each other, a pixel a12 and a pixel b12 are compared to each other, a pixel a13 and a pixel b13 are compared to each other, a pixel a14 and a pixel b14 are compared to each other, a pixel a15 and a pixel b15 are compared to each other, a pixel a16 and a pixel b16 are compared to each other, a pixel a17 and a pixel b17 are compared to each other, and a pixel a18 and a pixel b18 are compared to each other. Thus, all of the pixels a1 to a18 and the pixels b1 to b18, which show the surface to be inspected (the front face W1 of the work W), are compared to each other.

When the pixels a and b are compared to each other as described above, brightnesses B of the two pixels a and b individually selected are compared to each other on a set basis, thereby enabling inspections of all points shown by the pixels a and b over the entire front face W1 of the work W. More specifically, when there is no defect on the front face W1 of the work W, the brightnesses of the pixels a and b showing the surface to be inspected (the front face W1 of the work W) in the image A which has been photographed with the CCD camera 53 exhibit almost fixed values to be in a normal distribution of about ±20% when the front face W1 of the work W is a flat surface or a curved surface with a small curvature. On the other hand, when there are defects such as nonuniformity of color, smears, swells, hair cracks, chips or the like on the front face W1 of the work W, the brightnesses of the pixels a and b showing points where the defects exist exhibit unusual values. Accordingly, ratios between the brightnesses B of the pixels a and b showing the surface to be inspected (the front face W1 of the work W) are obtained, so that when all the ratios are within a predetermined range (when the brightnesses of the pixels are not outside the normal distribution of about ±20%), a judgement can be made that there is no defect on the front face W1 of the work W, while when there exist points whose ratio is outside the predetermined range (when there is a pixel having a brightness outside the normal distribution of about ±20%), a judgement can be made that the front face W1 of the work W is defect.

Generally, defects such as nonuniformity of color, smears, swells, hair cracks, chips or the like are often formed within a considerable range on the front face W1 of the work W, and therefore when defects such as nonuniformity of color, smears, swells, hair cracks, chips or the like exist, the brightnesses of the pixels a and b showing the surface to be inspected (the front face W1 of the work W) in the image A often continuously exhibit unusual values at a plurality of pixels a and b. Therefore, it is also adoptable to judge the state of the front face W1 of the work W to be defective when the ratios between the brightnesses B at a plurality of adjacent pixels a and b are outside the predetermined range.

Figure 7:
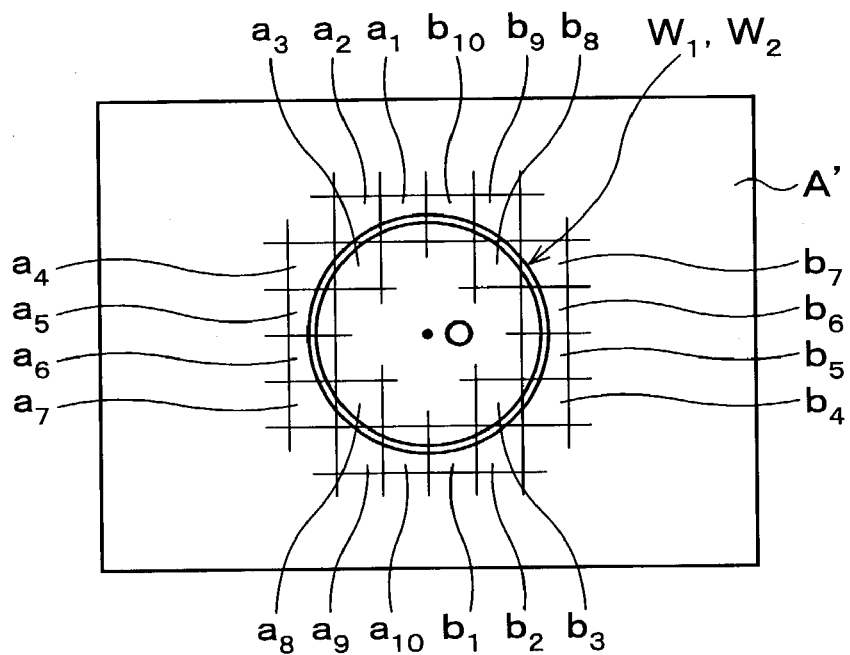
FIG. 7 is an explanatory view of a state of selecting two pixels which are point-symmetric about a center point of a work having a surface to be inspected in a circular shape when an outer peripheral part is inspected.

Subsequent to the inspection through the image photographed with the CCD camera 53 of the inspection means 26, the work W is illuminated by the light source 55 of the inspection means 27, and an image of the outer peripheral part of the front face W1 of the work W is photographed with the CCD camera 58 and inputted into the controller 70. An image A' of the outer peripheral part of the front face W1 of the work W thus photographed with the CCD camera 58 and inputted into the controller 70 presents a surface to be inspected (the outer peripheral part of the front face W1 of the work W) in a narrow continuous circular shape as shown in FIG. 7 when, for example, the front face W1 of the work W is in a circular shape, or presents a surface to be inspected (the outer peripheral part of the front face W1 of the work W) in a narrow continuous square shape as shown in FIG. 8 when, for example, the front face W1 of the work W is in a square shape.

Then, the controller 70 selects, similarly to the above, two arbitrary pixels a and b from among pixels showing the surface to be inspected (the outer peripheral part of the front face W1 of the work W) also in this image A' and compares the two pixels, thereby inspecting the outer peripheral part of the front face W1 of the work W. In this event, if the front face W1 of the work W is in a point-symmetric shape such as a circular shape, two pixels a and b which are point-symmetric about a center point O as shown in FIG. 7 are individually selected and compared to each other on a set basis. Specifically explaining the example shown in FIG. 7, a pixel a1 and a pixel b1 are compared to each other, a pixel a2 and a pixel b2 are compared to each other, a pixel a3 and a pixel b3 are compared to each other, a pixel a4 and a pixel b4 are compared to each other, a pixel a5 and a pixel b5 are compared to each other, a pixel a6 and a pixel b6 are compared to each other, a pixel a7 and a pixel b7 are compared to each other, a pixel a8 and a pixel b8 are compared to each other, a pixel a9 and a pixel b9 are compared to each other, and a pixel a10 and a pixel b10 are compared to each other. Thus, all of the pixels a1 to a10 and the pixels b1 to b10, which show the surface to be inspected (the outer peripheral part of the front face W1 of the work W), are compared to each other.

Figure 8:
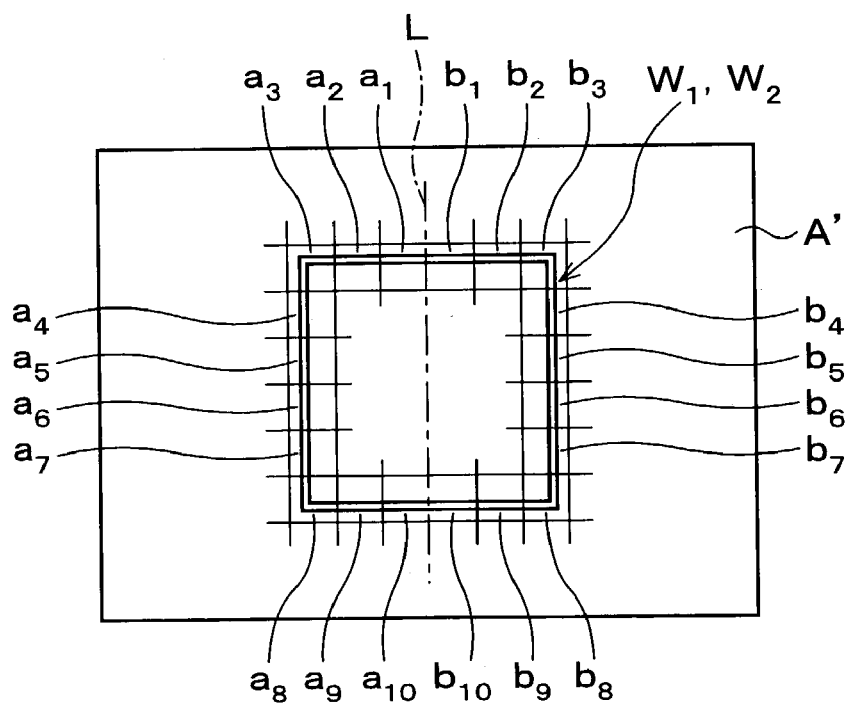
FIG. 8 is an explanatory view of a state of selecting two pixels which are line-symmetric about a center line of a work having a surface to be inspected in a square shape when an outer peripheral part is inspected.

If the front face W1 of the work W is in a line-symmetric shape such as a square shape, two pixels which are line-symmetric about a center line L as shown in FIG. 8 are individually selected and compared to each other. Specifically explaining the example shown in FIG. 8, a pixel a1 and a pixel b1 are compared to each other, a pixel a2 and a pixel b2 are compared to each other, a pixel a3 and a pixel b3 are compared to each other, a pixel a4 and a pixel b4 are compared to each other, a pixel a5 and a pixel b5 are compared to each other, a pixel a6 and a pixel b6 are compared to each other, a pixel a7 and a pixel b7 are compared to each other, a pixel a8 and a pixel b8 are compared to each other, a pixel a9 and a pixel b9 are compared to each other, and a pixel a10 and a pixel b10 are compared to each other. Thus, all of the pixels a1 to a10 and the pixels b1 to b10, which show the surface to be inspected (the outer peripheral part of the front face W1 of the work W), are compared to each other.

Also when the pixels a and b showing the outer peripheral part of the front face W1 of the work W are compared to each other as described above, brightnesses B of the two pixels a and b individually selected are similarly compared to each other, thereby enabling inspections of points shown by the pixels a and b of the outer peripheral part of the front face W1 of the work W. Also in this case, ratios between the brightnesses B of the pixels a and b showing the surface to be inspected (the outer peripheral part of the front face W1 of the work W) are obtained, so as to make it possible to judge, based on the ratios, whether or not there exists a defect on the outer peripheral part of the front face W1 of the work W. Further, it is also adoptable to judge the state of the outer peripheral part of the front face W1 of the work W to be defective when the ratios between the brightnesses B at a plurality of adjacent pixels a and b are outside the predetermined range.

Subsequent to the inspection through the image photographed with the CCD camera 58 of the inspection means 27 as described above, the work W is further illuminated by the light source 60 of the inspection means 28, and an image of the front face W1 of the work W is photographed with the CCD camera 63 and inputted into the controller 70. An image A of the front face W1 of the work W thus photographed with the CCD camera 63 and inputted into the controller 70 presents a surface to be inspected (the front face W1 of the work W) in a circular shape as previously explained with FIG. 5 when, for example, the front face W1 of the work W is in a circular shape, or presents a surface to be inspected (the front face W1 of the work W) in a square shape as previously explained with FIG. 6 when, for example, the front face W1 of the work W is a square shape.

Then, the controller 70 selects, similarly to the above, two arbitrary pixels a and b from among pixels showing the surface to be inspected (the front face W1 of the work W) also in this image A and compares the two pixels, thereby inspecting the front face W1 of the work W. In this event, if the front face W1 of the work W is in a point-symmetric shape such as a circular shape, as previously explained with FIG. 5, a pixel a1 and a pixel b1, a pixel a2 and a pixel b2, a pixel a3 and a pixel b3, a pixel a4 and a pixel b4, a pixel a5 and a pixel b5, a pixel a6 and a pixel b6, a pixel a7 and a pixel b7, a pixel a8 and a pixel b8, a pixel a9 and a pixel b9, a pixel a10 and a pixel b10, a pixel a11 and a pixel b11, a pixel a12 and a pixel b12, a pixel a13 and a pixel b13, a pixel a14 and a pixel b14, a pixel a15 and a pixel b15, and a pixel a16 and a pixel b16, which are point-symmetric about a center point O, are compared to each other respectively. Thus, all of the pixels a1 to a16 and the pixels b1 to b16, which show the surface to be inspected (the front face W1 of the work W), are compared to each other.

If the front face W1 of the work W is in a line-symmetric shape such as a square shape, as previously explained with FIG. 6, a pixel a1 and a pixel b1, a pixel a2 and a pixel b2, a pixel a3 and a pixel b3, a pixel a4 and a pixel b4, a pixel a5 and a pixel b5, a pixel a6 and a pixel b6, a pixel a7 and a pixel b7, a pixel a8 and a pixel b8, a pixel a9 and a pixel b9, a pixel a10 and a pixel b10, a pixel a11 and a pixel b11, a pixel a12 and a pixel b12, a pixel a13 and a pixel b13, a pixel a14 and a pixel b14, a pixel a15 and a pixel b15, a pixel a16 and a pixel b16, a pixel a17 and a pixel b17, and a pixel a18 and a pixel b18, which are line-symmetric about a center line L, are compared to each other respectively. Thus, all of the pixels a1 to a18 and the pixels b1 to b18, which show the surface to be inspected (the front face W1 of the work W), are compared to each other.

In this case, the light source 60, the conversion lens 61, the zoom lens 62, and the CCD camera 63 are all disposed at an angle with respect to the front face W1 of the work W in the inspection means 28, so that, for example, if there are projections and depressions on the front face W1 of the work W, light and shade appear at the pixels a and b showing the surface to be inspected (the front face W1 of the work W) due to the projections and depressions.

This allows the controller 70 to judge the presence or absence of projections and depressions on the front face W1 of the work W through the image photographed with the CCD camera 63 of the inspection means 28. Also in this case, ratios between the brightnesses B of the pixels a and b showing the surface to be inspected (the front face W1 of the work W) are individually obtained, so as to make it possible to judge, based on the ratios, whether or not there exist defects (projections and depressions) on the front face W1 of the work W. Further, it is also adoptable to judge the state of the front face W1 of the work W to be defective when the ratios between the brightnesses B at a plurality of adjacent pixels a and b are outside the predetermined range.

As described above, the appearance on the side of the front face W1 of the work W is comprehensively inspected by the inspection means 26, 27 and 28 during the carriage by the first conveyer 14. After the respective inspections by the inspection means 26, 27 and 28, the work W is carried to the termination part of the first conveyer 14 and reversed, turned over, by the reversing apparatus 21, the work W which has been brought into the attitude that its back face W2 directs upward is fed to the start part of the second conveyer 20. Then, the work W with its back face W2 directing upward is carried rightward in FIG. 1 by the second conveyer 20.

During the carriage by the second conveyer 20, the inspections on the side of the back face W2 of the work W are conducted by the inspection means 35, 36 and 37 respectively similarly to the inspections on the side of the front face W1 of the work W which have previously been conducted by the inspection means 26, 27 and 28. As described above, the states on the side of the front face W1 and the side of the back face W2 of the work W are comprehensively judged by the controller 70. When the works W, whose appearances on both sides of the front face W1 and the back face W2 have been inspected, are carried to the termination part of the second conveyer 20, the sorter 38 sorts, by the control of the controller 70, the works W in such a manner to carry out only the works W having a normal appearance to the storage region 41. Therefore, this inspection system 1 makes it possible to easily inspect the presence or absence of defects in shape such as chips, cracks, projections and depressions or the like on the front face W1 and the back face W2 of the work W and their outer peripheral parts, so that only the works W having a normal appearance without defects can be selectively obtained.

An example of the preferred embodiment of the present invention has been explained, but the present invention is not limited to the above-described embodiment. The article under inspection is not limited to the work W such as a rare earth magnet or the like, and the present invention is applicable to appearance inspections of other various kinds of articles. Further, any one of the inspection means 26, 27 and 28 may be disposed along the first conveyer 14, and the inspection means 26, 27 and 28 may be disposed along the first conveyer 14 in any combination. Similarly, any one of the inspection means 35, 36 and 37 may be disposed along the second conveyer 20, and the inspection means 35, 36 and 37 may be disposed along the second conveyer 20 in any combination.

Generally, an illumination light source is provided adjacent to the CCD camera because the surface to be inspected of an article under inspection changes in brightness depending on its color tone, roughness, the presence or absence of plating and so on. The light source may employ a typical illumination such as a fluorescent tube or the like, and it is preferable to uniformly illuminate the surface to be inspected from above with a brightness of 500 lux to 20000 lux by a ring-shaped halogen lamp. As for the CCD camera, a color CCD camera is necessary for inspection of the color tone, but a monochrome CCD camera sufficiently serves for inspection of the surface of a rare-metal sintered magnet and so on. The CCD camera needs 300 thousands pixels or more, preferably a million pixels or more, and since as the pixels increases in number, the CCD camera can inspect more finely the surface but increases in nose, it is necessary to select a CCD camera in accordance with the condition of inspections.

Generally, the CCD camera photographs an image with the aperture fully opened. An image is preferably photographed at a shutter speed of $1/1000$ sec to $1/10000$ sec. Note that if the surface to be inspected is in a point-symmetric shape such as a circular shape, it is preferable to individually select two pixels which are point-symmetric about a center point O as explained with FIG. 5 and compare them. If the surface to be inspected is in a line-symmetric shape such as a square shape, it is preferable to individually select two pixels which are line-symmetric about a center line L as explained with FIG. 6 and compare them.

According to the realization of the present inventors, when an inspection is conducted by comparing the brightnesses of the two selected pixels, the ratio between the brightnesses ranges from 0.7 to 1.3 can be safely judged to be normal. The range of the ratio between the brightnesses judged to be normal can be arbitrarily set in accordance with the kind of inspection. If the range is too narrow, there are worries that non-defectives are judged to be defectives, and if the range is too wide, there are worries that defectives are judged to be non-defectives. In consideration of the above circumstances in advance, a threshold value for judging defectives needs to be appropriately set and incorporated in a decision program for decision whether non-defective or defective. The series of operations are performed by a program installed in the controller, which allows appearance inspections to be conducted efficiently in sequence. Further, the judgement is designed to sort articles not only into two levels of non-defectives and defectives but also into three levels or more, so that inspections are repeated or visual inspections are partially introduced, which enables more detailed inspections.

EXAMPLE

In the inspection system of the present invention which has been explained in FIG. 1 and so on, a Nd—Fe—B—C sintered magnet in a disc shape of 6.5 mm in diameter and 1.0 mm in thickness was employed as a work, and its appearance was sequentially inspected while the work was carried at a fixed speed of 50 mm/sec. CS-3910 CCD camera (with 1.41 million pixels) manufactured by TOKYO ELECTRONIC INDUSTRY with MS-501 high resolution lens manufactured by SEIWA OPTICAL was used, and a ring-shaped halogen lamp HL-28-2000 (28φ) manufactured by SEIWA OPTICAL was used as a light source. The external diameter of the work was subjected to an envelope process to obtain its shape, so that the work was photographed when the center of the shape came to a position under the center of the CCD camera. The aperture was fully opened and the shutter speed was 1/2000 sec. Pixels in point-symmetry were selected, and the ratio between their brightnesses was equal to or more than 1.4 was regarded as abnormal, so that the setting was made such that the appearance of a work was judged to be defective when 450 or more abnormal pixels exist continuously. The inspection according to the present invention was performed on a thousand works. A visual inspection was also performed on a test which was conducted on the embodied example, and results by the visual inspection were regarded as correct.

Further, in an inspection method of a comparison example, pixels at about ten points were selected from among pixels showing a surface to be inspected in an image photographed with a CCD camera, and a mean value of brightnesses thereof was set as a standard value, so that the brightness of a pixel at a point to be measured was compared to the standard value, thereby inspecting the state of a surface of an article. The comparison between the embodied example of the present invention and the comparison example resulted in Table 1, in which the embodied example of the present invention was superior to the comparison example in both the accuracy rate of non-defectives and the accuracy rate of defectives.

TABLE 1

|  | Non-defectives | Accuracy Rate | Defectives | Accuracy Rate | Total Accuracy Rate |
| --- | --- | --- | --- | --- | --- |
| Embodied Example | 940 | 99.5% | 60 | 62.5% | 97.3% |
| Comparison Example | 875 | 95.0% | 125 | 40.0% | 88.1% |
| Visual Inspection | 950 | 100% | 50 | 100% | 100% |

What is claimed is:

1. A method for inspecting a surface of an article through an image thereof, comprising the steps of:
   photographing a surface to be inspected of said article with a CCD camera;
   selecting two arbitrary pixels in point-symmetry or line symmetry from among pixels showing the surface to be inspected in the image; and
   comparing the two pixels to each other to inspect the surface of said article.

2. The inspection method as set forth in claim 1, wherein all of the pixels showing the surface to be inspected are compared.

3. The inspection method as set forth in claim 2, wherein brightnesses of the two selected pixels are compared.

4. The inspection method as set forth in claim 3, wherein a ratio between the brightnesses of the two selected pixels is obtained, and when a predetermined number of pixels having ratios outside a predetermined range exist continuously, a state of the surface of said article is judged to be defective.

5. The inspection method as set forth in claim 1, wherein when the surface to be inspected of said article is photographed with the CCD camera, the surface to be inspected is illuminated by a light source.

6. A system for inspecting a surface of an article through an image thereof, comprising:
   a light source for illuminating a surface to be inspected of said article;
   a CCD camera for photographing the surface to be inspected of said article; and
   a controller for selecting two arbitrary pixels in point-symmetry or line symmetry from among pixels showing the surface to be inspected in the photographed image and comparing the two pixels to each other to inspect the surface of said article.

7. The inspection system as set forth in claim 6, further comprising:
   a sorter for sorting said articles in accordance with inspection results by said controller.

* * * * *